US008529628B2

(12) United States Patent
Marino et al.

(10) Patent No.: US 8,529,628 B2
(45) Date of Patent: Sep. 10, 2013

(54) EXPANDING INTERVERTEBRAL DEVICE AND METHODS OF USE

(75) Inventors: James F. Marino, La Jolla, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 527 days.

(21) Appl. No.: 12/797,498

(22) Filed: Jun. 9, 2010

(65) Prior Publication Data

US 2011/0004308 A1 Jan. 6, 2011

Related U.S. Application Data

(60) Provisional application No. 61/218,009, filed on Jun. 17, 2009.

(51) Int. Cl.
*A61F 2/44* (2006.01)
(52) U.S. Cl.
USPC .................................. 623/17.16; 623/17.11
(58) Field of Classification Search
USPC .... 606/86 A, 246–248, 279, 911; 623/17.11, 623/17.13, 17.16, 901, 926
See application file for complete search history.

(56) References Cited

U.S. PATENT DOCUMENTS

| 3,108,593 A | 10/1963 | Glassman |
| 3,800,788 A | 4/1974 | White |
| 3,846,846 A | 11/1974 | Fischer |
| 3,867,728 A | 2/1975 | Stubstad et al. |
| 4,475,856 A | 10/1984 | Toomingas |
| 4,973,301 A | 11/1990 | Nissenkorn |
| 5,059,193 A * | 10/1991 | Kuslich .................... 606/247 |
| 5,108,395 A | 4/1992 | Laurain |
| 5,123,926 A | 6/1992 | Pisharodi |
| 5,167,665 A | 12/1992 | McKinney |
| 5,171,248 A | 12/1992 | Ellis |
| 5,171,278 A | 12/1992 | Pisharodi |
| 5,263,953 A | 11/1993 | Bagby |
| 5,306,310 A | 4/1994 | Siebels |
| 5,390,683 A | 2/1995 | Pisharodi |
| 5,402,772 A | 4/1995 | Moll et al. |
| 5,454,365 A | 10/1995 | Bonutti |
| 5,456,667 A * | 10/1995 | Ham et al. ................ 604/107 |
| 5,518,498 A | 5/1996 | Lindenberg et al. |
| 5,549,679 A | 8/1996 | Kuslich |
| 5,571,189 A | 11/1996 | Kuslich |

(Continued)

FOREIGN PATENT DOCUMENTS

| EP | 1529494 A1 | 5/2005 |
| FR | 2717068 A1 | 9/1995 |

(Continued)

*Primary Examiner* — Nicholas Woodall
*Assistant Examiner* — Larry E Waggle, Jr.
(74) *Attorney, Agent, or Firm* — Fred C. Hernandez; Mintz Levin Cohn Ferris Glovsky and Popeo, P.C.

(57) ABSTRACT

Disclosed is a spinal stabilization device having a plurality of elongate arms having a distal end portion and a proximal end portion, wherein the elongate arms define an interior volume between the distal end portion and the proximal end portion; at least one limit band coupled circumferentially to one or more of the plurality of elongate arms; and a tensioning element positioned within the interior volume. The plurality of elongate arms can transition from a constrained, delivery configuration that is radially contracted and axially elongated to a relaxed, deployment configuration that is radially expanded and axially shortened.

46 Claims, 13 Drawing Sheets

(56) References Cited

U.S. PATENT DOCUMENTS

| | | | |
|---|---|---|---|
| 5,575,790 A | 11/1996 | Chen et al. | |
| 5,578,035 A | 11/1996 | Lin | |
| 5,591,197 A | 1/1997 | Orth et al. | |
| 5,702,448 A | 12/1997 | Buechel et al. | |
| 5,725,341 A | 3/1998 | Hofmeister | |
| 5,749,916 A | 5/1998 | Richelsoph | |
| 5,759,186 A | 6/1998 | Bachmann et al. | |
| 5,782,832 A | 7/1998 | Larsen et al. | |
| 5,782,838 A | 7/1998 | Beyar et al. | |
| 5,827,289 A | 10/1998 | Reiley | |
| 5,843,158 A * | 12/1998 | Lenker et al. | 623/1.13 |
| 5,876,457 A | 3/1999 | Picha et al. | |
| 5,897,557 A | 4/1999 | Chin et al. | |
| 5,972,015 A | 10/1999 | Scribner et al. | |
| 5,976,187 A | 11/1999 | Richelsoph | |
| 5,989,291 A | 11/1999 | Ralph et al. | |
| 6,019,789 A | 2/2000 | Dinh et al. | |
| 6,019,793 A | 2/2000 | Perren | |
| 6,039,761 A | 3/2000 | Li et al. | |
| 6,056,749 A | 5/2000 | Kuslich | |
| 6,086,589 A | 7/2000 | Kuslich et al. | |
| 6,126,689 A | 10/2000 | Brett | |
| 6,127,597 A | 10/2000 | Beyar et al. | |
| 6,149,651 A | 11/2000 | Drewry et al. | |
| 6,193,757 B1 | 2/2001 | Foley et al. | |
| 6,200,349 B1 | 3/2001 | Naybour | |
| 6,206,923 B1 | 3/2001 | Boyd et al. | |
| 6,214,037 B1 | 4/2001 | Mitchell et al. | |
| 6,217,608 B1 | 4/2001 | Penn et al. | |
| 6,245,101 B1 | 6/2001 | Drasler et al. | |
| 6,248,110 B1 | 6/2001 | Reiley | |
| 6,261,289 B1 | 7/2001 | Levy | |
| 6,383,188 B2 | 5/2002 | Kuslich et al. | |
| 6,395,031 B1 | 5/2002 | Foley et al. | |
| 6,409,766 B1 | 6/2002 | Brett | |
| 6,447,478 B1 | 9/2002 | Maynard | |
| 6,488,710 B2 * | 12/2002 | Besselink | 623/17.15 |
| 6,500,182 B2 | 12/2002 | Foster | |
| 6,551,319 B2 * | 4/2003 | Lieberman | 623/17.11 |
| 6,554,833 B2 | 4/2003 | Levy et al. | |
| 6,562,074 B2 | 5/2003 | Gerbec et al. | |
| 6,582,467 B1 | 6/2003 | Teitelbaum et al. | |
| 6,620,162 B2 | 9/2003 | Kuslich et al. | |
| 6,620,169 B1 | 9/2003 | Peterson et al. | |
| 6,666,891 B2 | 12/2003 | Boehm, Jr. et al. | |
| 6,676,665 B2 | 1/2004 | Foley et al. | |
| 6,712,853 B2 | 3/2004 | Kuslich | |
| 6,773,460 B2 | 8/2004 | Jackson | |
| 6,780,175 B1 | 8/2004 | Sachdeva et al. | |
| 6,833,006 B2 | 12/2004 | Foley et al. | |
| 6,893,464 B2 | 5/2005 | Kiester | |
| 6,960,215 B2 | 11/2005 | Olson, Jr. et al. | |
| 6,962,606 B2 | 11/2005 | Michelson | |
| 6,969,404 B2 | 11/2005 | Ferree | |
| 7,052,498 B2 | 5/2006 | Levy et al. | |
| 7,083,650 B2 | 8/2006 | Moskowitz et al. | |
| 7,097,648 B1 | 8/2006 | Globerman et al. | |
| 7,128,760 B2 | 10/2006 | Michelson | |
| 7,166,121 B2 | 1/2007 | Reiley et al. | |
| 7,189,235 B2 | 3/2007 | Cauthen | |
| 7,211,073 B2 | 5/2007 | Fitzgerald et al. | |
| 7,214,243 B2 | 5/2007 | Taylor | |
| 7,217,293 B2 | 5/2007 | Branch, Jr. | |
| 7,297,146 B2 | 11/2007 | Braun et al. | |
| 7,655,042 B2 | 2/2010 | Foley et al. | |
| 7,722,674 B1 | 5/2010 | Grotz | |
| 7,819,921 B2 | 10/2010 | Grotz | |
| 7,892,286 B2 | 2/2011 | Michelson | |
| 7,963,970 B2 | 6/2011 | Marino | |
| 7,985,256 B2 | 7/2011 | Grotz et al. | |
| 7,993,403 B2 | 8/2011 | Foley et al. | |
| 8,043,376 B2 | 10/2011 | Falahee | |
| 8,070,813 B2 | 12/2011 | Grotz et al. | |
| 8,105,382 B2 | 1/2012 | Olmos et al. | |
| 8,123,807 B2 | 2/2012 | Kim | |
| 2002/0026197 A1 | 2/2002 | Foley et al. | |
| 2003/0074075 A1 | 4/2003 | Thomas, Jr. et al. | |
| 2003/0083746 A1 | 5/2003 | Kuslich | |
| 2004/0010315 A1 | 1/2004 | Song | |
| 2004/0097930 A1 | 5/2004 | Justis et al. | |
| 2004/0153064 A1 | 8/2004 | Foley et al. | |
| 2004/0193158 A1 | 9/2004 | Lim et al. | |
| 2005/0038447 A1 | 2/2005 | Huffmaster | |
| 2005/0060023 A1 | 3/2005 | Mitchell et al. | |
| 2005/0113838 A1 | 5/2005 | Phillips et al. | |
| 2005/0131417 A1 | 6/2005 | Ahern et al. | |
| 2005/0143827 A1 | 6/2005 | Globerman et al. | |
| 2005/0182417 A1 | 8/2005 | Pagano | |
| 2005/0197711 A1 | 9/2005 | Cachia | |
| 2005/0222681 A1 * | 10/2005 | Richley et al. | 623/17.11 |
| 2006/0009844 A1 | 1/2006 | Bloemer et al. | |
| 2006/0036323 A1 | 2/2006 | Carl et al. | |
| 2006/0064094 A1 | 3/2006 | Levy et al. | |
| 2006/0084985 A1 | 4/2006 | Kim | |
| 2006/0084998 A1 | 4/2006 | Levy et al. | |
| 2006/0100706 A1 | 5/2006 | Shadduck et al. | |
| 2006/0136065 A1 | 6/2006 | Gontarz et al. | |
| 2006/0155379 A1 | 7/2006 | Heneveld et al. | |
| 2006/0167547 A1 | 7/2006 | Suddaby | |
| 2006/0235417 A1 | 10/2006 | Sala | |
| 2006/0271061 A1 | 11/2006 | Beyar et al. | |
| 2006/0271197 A1 | 11/2006 | Saal et al. | |
| 2007/0043440 A1 * | 2/2007 | William et al. | 623/17.11 |
| 2007/0050033 A1 | 3/2007 | Reo et al. | |
| 2007/0067034 A1 * | 3/2007 | Chirico et al. | 623/17.11 |
| 2007/0088436 A1 | 4/2007 | Parsons et al. | |
| 2007/0118171 A1 | 5/2007 | Reiley et al. | |
| 2007/0118222 A1 | 5/2007 | Lang | |
| 2007/0150063 A1 | 6/2007 | Ruberte et al. | |
| 2007/0162044 A1 | 7/2007 | Marino | |
| 2007/0162127 A1 | 7/2007 | Peterman et al. | |
| 2007/0173939 A1 | 7/2007 | Kim et al. | |
| 2007/0198013 A1 | 8/2007 | Foley et al. | |
| 2007/0198088 A1 | 8/2007 | Biedermann et al. | |
| 2007/0219634 A1 | 9/2007 | Greenhalgh et al. | |
| 2007/0270959 A1 | 11/2007 | Dubousset | |
| 2007/0282443 A1 | 12/2007 | Globerman et al. | |
| 2008/0009875 A1 | 1/2008 | Sankaran et al. | |
| 2008/0009876 A1 | 1/2008 | Sankaran et al. | |
| 2008/0009877 A1 | 1/2008 | Sankaran et al. | |
| 2008/0065143 A1 | 3/2008 | Reiley et al. | |
| 2008/0071356 A1 | 3/2008 | Greenhalgh et al. | |
| 2008/0086212 A1 | 4/2008 | Zucherman et al. | |
| 2008/0114367 A1 | 5/2008 | Meyer et al. | |
| 2008/0140203 A1 | 6/2008 | Davis | |
| 2008/0147192 A1 | 6/2008 | Edidin et al. | |
| 2008/0147194 A1 | 6/2008 | Grotz et al. | |
| 2008/0154305 A1 | 6/2008 | Foley et al. | |
| 2008/0161933 A1 | 7/2008 | Grotz et al. | |
| 2008/0183204 A1 * | 7/2008 | Greenhalgh et al. | 606/198 |
| 2008/0228028 A1 | 9/2008 | Carlson et al. | |
| 2008/0281364 A1 | 11/2008 | Chirico et al. | |
| 2009/0005821 A1 | 1/2009 | Chirico et al. | |
| 2009/0012564 A1 | 1/2009 | Chirico et al. | |
| 2009/0024157 A1 | 1/2009 | Anukhin | |
| 2009/0024166 A1 | 1/2009 | Carl et al. | |
| 2009/0036799 A1 | 2/2009 | Sandhu et al. | |
| 2009/0054935 A1 | 2/2009 | Miller et al. | |
| 2009/0216331 A1 | 8/2009 | Grotz et al. | |
| 2009/0312764 A1 | 12/2009 | Marino | |
| 2010/0057204 A1 | 3/2010 | Kadaba et al. | |
| 2010/0145455 A1 | 6/2010 | Simpson et al. | |
| 2010/0145456 A1 | 6/2010 | Simpson et al. | |
| 2010/0305705 A1 | 12/2010 | Butler et al. | |
| 2011/0009869 A1 | 1/2011 | Marino et al. | |
| 2011/0137420 A1 | 6/2011 | Michelson | |

FOREIGN PATENT DOCUMENTS

| | | |
|---|---|---|
| GB | 2268068 A | 1/1994 |
| WO | WO 2005/048856 | 6/2005 |
| WO | WO-2009152256 A2 | 12/2009 |

* cited by examiner

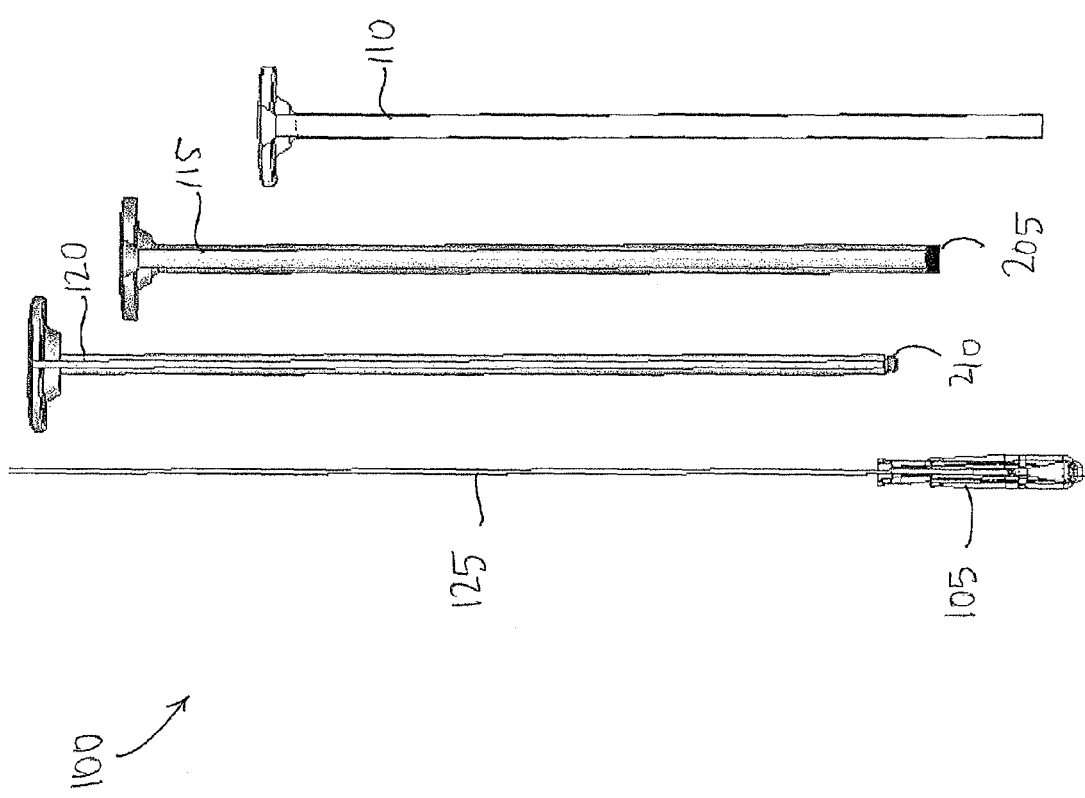

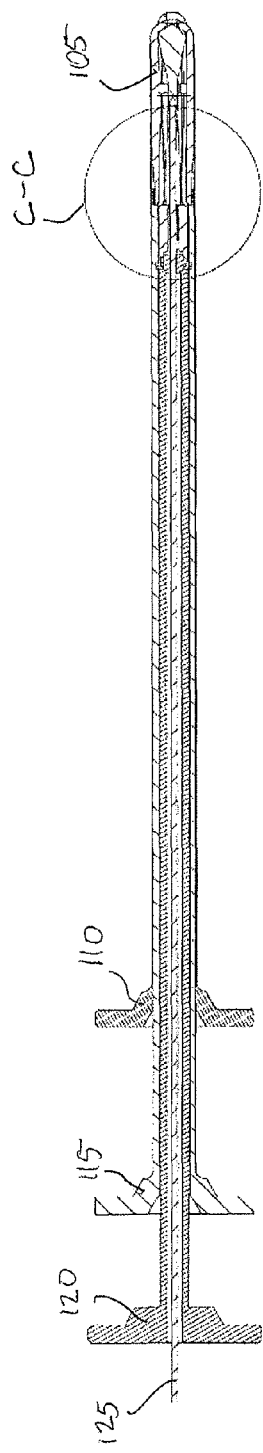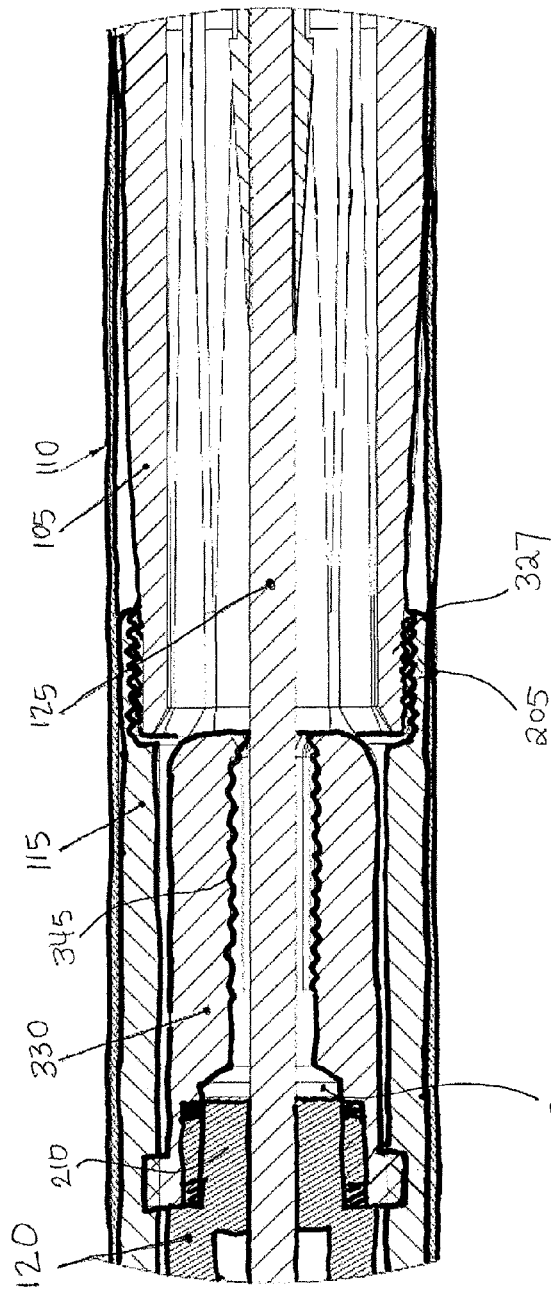

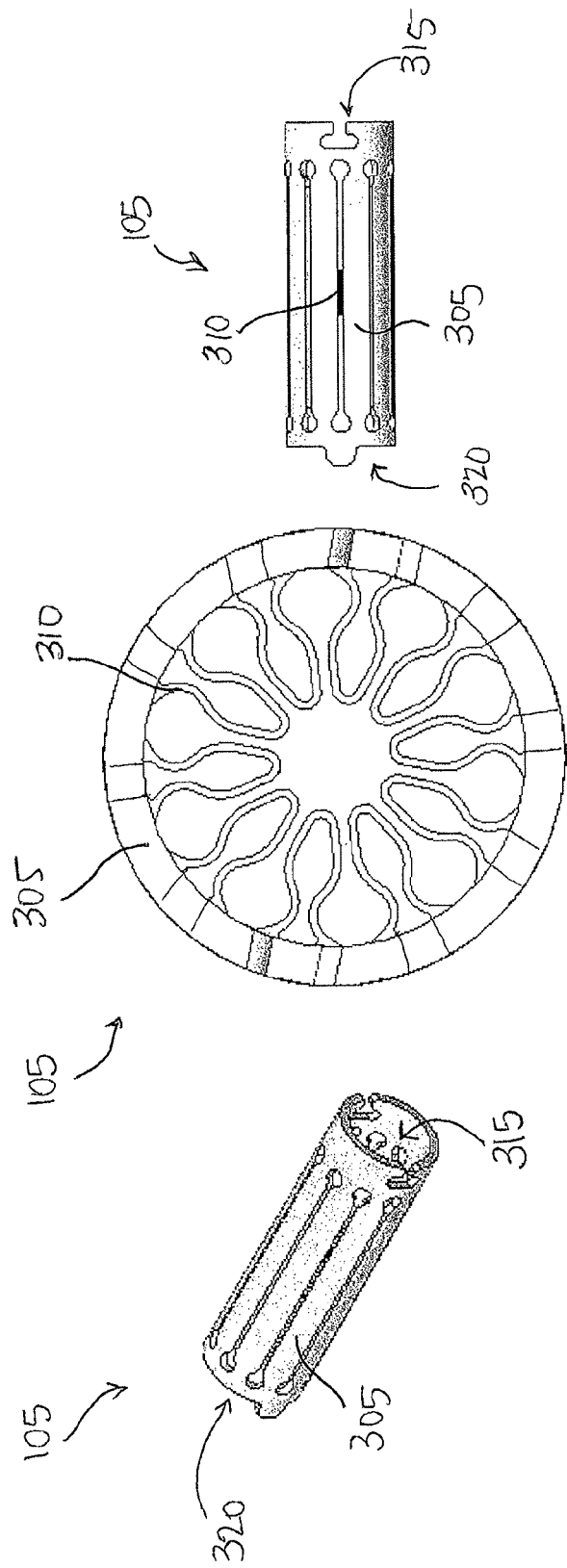

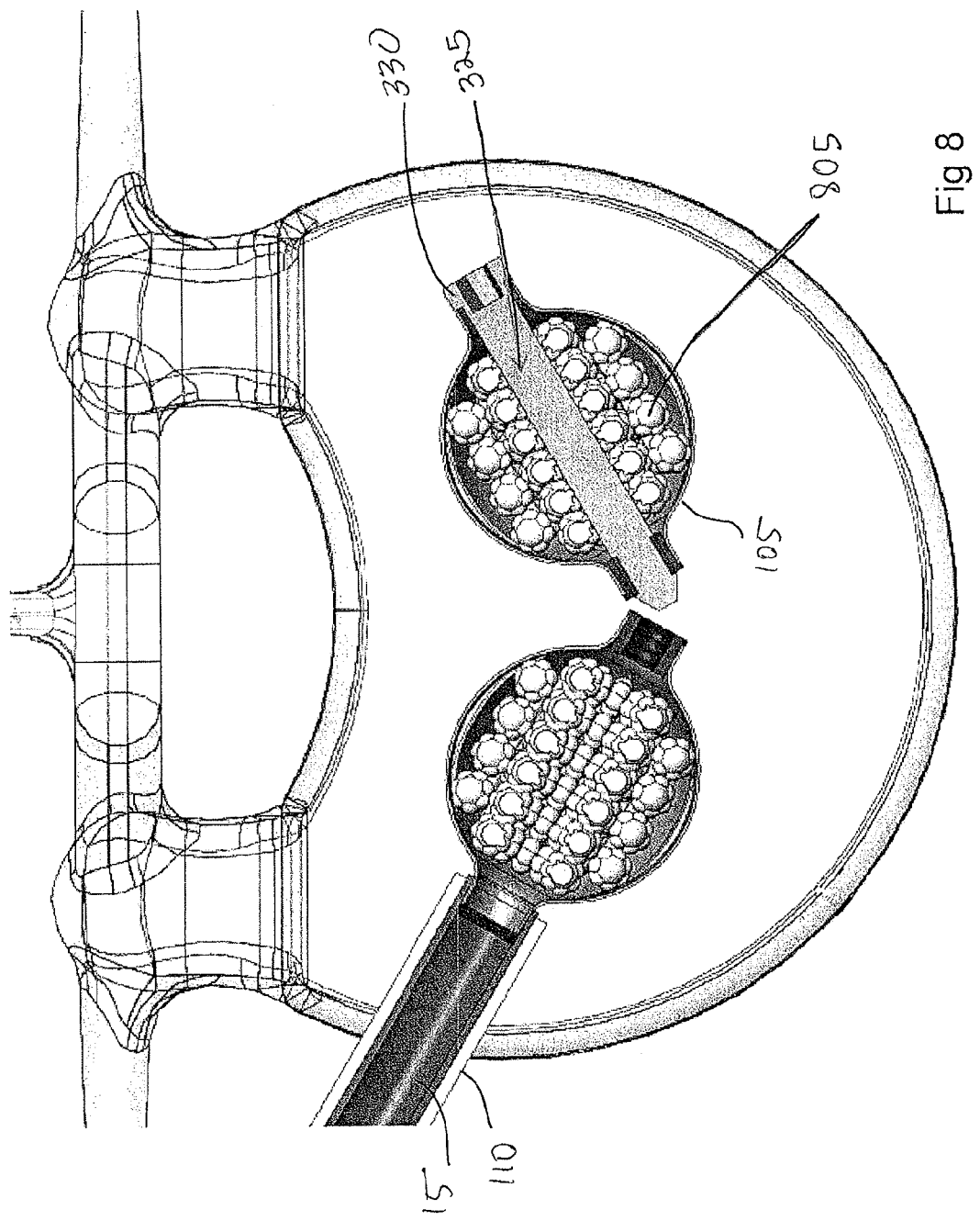

EXPANDING INTERVERTEBRAL DEVICE AND METHODS OF USE

REFERENCE TO PRIORITY DOCUMENT

This application claims the benefit of priority under 35 U.S.C. §119(e) of U.S. Provisional Application Ser. No. 61/218,009, filed Jun. 17, 2009. Priority of the filing date of Jun. 17, 2009, is hereby claimed and the disclosure of the above-noted application is incorporated by reference in its entirety by reference thereto.

BACKGROUND

A significant number of adults have had an episode of back pain or suffer chronic back pain emanating from a region of the spinal column. A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. Many people suffering from back pain resort to surgical intervention to alleviate their pain.

Disc degeneration can contribute to back pain. With age, the nucleus pulposus of the intervertebral discs tends to become less fluid and more viscous. Dehydration of the intervertebral disc and other degenerative effects can cause severe pain. Annular fissures also may be associated with a herniation or rupture of the annulus causing the nucleus to bulge outward or extrude out through the fissure and impinge upon the spinal column or nerves (a "ruptured" or "slipped" disc).

In addition to spinal deformities that can occur over several motion segments, spondylolisthesis (forward displacement of one vertebra over another, usually in the lumbar or cervical spine) is associated with significant axial and/or radicular pain. Patients who suffer from such conditions can experience diminished ability to bear loads, loss of mobility, extreme and debilitating pain, and oftentimes suffer neurological deficit in nerve function.

Failure of conservative therapies to treat spinal pain such as for example bed rest, pain and muscle relaxant medication, physical therapy or steroid injection often urges patients to seek spinal surgical intervention. Many surgical techniques, instruments and spinal disc implants have been described that are intended to provide less invasive, percutaneous, or minimally-invasive access to a degenerated intervertebral spinal disc. Instruments are introduced through the annulus for performing a discectomy and implanting bone growth materials or biomaterials or spinal disc implants within the annulus. One or more annular incisions are made into the disc to receive spinal disc implants or bone growth material to promote fusion, or to receive a pre-formed, artificial, functional disc replacement implant.

Extensive perineural dissection and bone preparation can be necessary for some of these techniques. In addition, the disruption of annular or periannular structures can result in loss of stability or nerve injury. As a result, the spinal column can be further weakened and/or result in surgery-induced pain syndromes.

SUMMARY

The present disclosure relates to methods, systems and devices for stabilizing and fusing bony structures and for maintaining the space during postoperative healing.

In an embodiment, disclosed is a spinal stabilization device having a plurality of elongate arms having a distal end portion and a proximal end portion. The elongate arms define an interior volume between the distal end portion and the proximal end portion. The device also has a limit band coupled circumferentially to the plurality of elongate arms; and a tensioning element positioned within the interior volume. The plurality of elongate arms passively transition from a constrained, delivery configuration that is radially contracted and axially elongated to a relaxed, deployment configuration that is radially expanded and axially shortened and configured to be released within an intervertebral disc space.

The limit band can be integral with one or more of the plurality of elongate arms or the limit band can be a separate unitary element coupled to an outer circumference of the device. The limit band can be radially contracted when the plurality of elongate arms are in the delivery configuration and the limit band can be radially expanded when the plurality of elongate arms are in the deployed configuration. The limit band can resist splaying of the plurality of arms when in the deployed configuration and the device is under a lateral wall load.

The tensioning element can include a linkage rod and a locking end cap. The linkage rod can include a distal end and a proximal end. The distal end of the linkage rod can couple to the distal end portion of the elongate arms and the proximal end of the linkage rod can couple to the locking end cap. The locking end cap can be coupled to the proximal end portion of the elongate arms. The proximal end of the linkage rod can be threaded and couple to complementary threads of the locking end cap. The tensioning element can lock the distal end portion of the arms and the proximal end portions of the arms when the arms are in the deployed configuration. Compressive loads directed perpendicular to the elongate arms can result in a tensile load on the tensioning element. Applied circumferential, inward force can urge the plurality of arms into the delivery configuration.

The interior volume in the deployed configuration can be a fusiform, tubular, oblong, or spheroid shape. The deployed configuration of the plurality of elongate arms can be a whisk, coil, spring, chain-link, or woven basket shape. The interior volume can be filled with one or more therapeutic materials including bone growth material, bone graft material, bone void filler, cancellous bone graft, cortical bone graft, cancellous bone fragment, cortical bone fragment, osteoconductive material, osteoproliferative material, osteoinductive material, a bone morphogenic cytokine, BMP-2, collagen sponge soaked in bone material, or BMP-2 soaked collagen sponge. The tensioning element can seal the interior volume at the distal end portion and the proximal end portion. The tensioning element can radially displace and distribute the therapeutic material within the interior volume.

The plurality of elongate arms can be nitinol, titanium/nickel alloy, or a polymeric material. The plurality of elongate arms can have a wall thickness and/or width that is non-uniform. The plurality of elongate arms can have a reduced wall thickness where the arms couple to the limit band. The plurality of elongate arms can have a reduced width where the arms couple to the limit band. The external diameter of the device in the constrained, delivery configuration can be generally constant.

An another aspect, disclosed is a vertebral interbody fusion system having an interbody device, a tensioning element, and a cannula assembly. The interbody device includes a plurality of elongate arms having a distal end portion and a proximal end portion. The elongate arms define an interior volume between the distal end portion and the proximal end portion of the interbody device, and at least one limit band coupled circumferentially to one or more of the plurality of elongate arms. The interbody device is capable of transitioning from a constrained, delivery configuration that is radially contracted and axially elongated to a relaxed, deployed configuration that is radially expanded and axially shortened. The tensioning element is positioned within the interior volume and includes a linkage rod and a locking end cap. The cannula assembly is configured to couple to the interbody device. The cannula assembly includes a slidable containment sleeve having a lumen sized to contain the interbody device in the delivery configuration, a control sleeve having a distal coupling element that couples to the proximal end portion of the interbody device, and a locking driver element. The interbody device transitions from the delivery configuration to the deployed configuration upon proximal withdrawal of the containment sleeve. The cannula assembly can be configured to reversibly couple to the interbody device. The distal coupling element of the control sleeve can reversibly couple to the proximal end portion of the interbody device.

In another aspect, disclosed is a method of manufacturing a spinal stabilization device. The method includes providing a tubular element having an inner passageway and an axial length, the tubular element being made of a shape memory material; providing a laser system; removing portions of the tubular element with the laser system using cut lines parallel to the axial length of the tubular element, wherein removing portions defines openings through the element and creates a plurality of elongate, axially-aligned flexible arms surrounding the inner passageway having a first thickness and a plurality of spaces between the arms; removing a layer of material from the arms with the laser system using cut lines transverse to the axial length of the tubular element, wherein removing the layer of material creates regions of the arms having a second thickness that is thinner than the first thickness; setting the shape memory of the tubular element in a radially expanded, axially foreshortened configuration; coupling a flexible, limit band circumferentially to the plurality of arms to the regions of the arms having the second thickness; and compressing the tubular element into a radially contracted, axially elongated configuration. Compressing the tubular element can include cooling the tubular element. Setting the shape memory can include heat-setting the shape memory of the tubular element. The shape memory material can be nitinol, titanium/nickel alloy, or a polymeric material. The arms can be self-expanding.

Other features and advantages of the present invention should be apparent from the following description of various embodiments, which illustrate, by way of example, the principles of the invention.

BRIEF DESCRIPTION OF THE DRAWINGS

FIG. 2A shows a cross-sectional, exploded view of an embodiment of an interbody fusion device and system.

FIG. 2B shows a cross-sectional view of an embodiment of an interbody fusion device and system.

FIG. 2C shows a close-up view of FIG. 2B taken along circle C-C.

FIGS. 3A-3C show perspective, front and side views of an embodiment of an interbody device in a radially contracted, axially elongated configuration.

FIG. 8 shows another embodiment of an interbody device in a radially expanded, axially shortened configuration that is tensioned and filled with bone graft material.

DETAILED DESCRIPTION

Disclosed is an interbody system that is adapted to stabilize and fuse bony structures. The devices and fusion systems described herein are designed for minimally-invasive interbody fusion procedures and can be releasably deployed through a variety of minimally-invasive access channels or small access ports and into the intervertebral disc space, for example. The devices and systems described herein can be used for a variety of surgical applications.

The interbody devices described herein can be self-expanding such that they are actively collapsed to a low profile prior to delivery, such as with an outer sheath and then allowed to relax or expand into a higher profile upon insertion between bony structures and removal of the outer, compressive forces. The initial collapsed configuration can be accomplished in various ways, as will be described in more detail below, such as by delivering the interbody device using a confining sleeve or sheath or restraining ring such that the interbody device is compressed or restrained to the low profile. Once introduced into the target location, the restraining element such as a confining sleeve or ring can be withdrawn along the axis of introduction such that the interbody device can assume its volumetrically enlarged geometry. The volumetrically enlarged geometry of the interbody devices described herein is characterized by foreshortening of the axial length as the outer dimensions radially expand. Conversely, the interbody devices described herein can axially lengthen upon radial compression. The volumetric increase is a result conformational changes in the "defining" perimeter and not as a result of an elastomeric expansion. It should be appreciated that no filling of the interior of the device with other materials is required in order to expand the device. It should also be appreciated that the interbody devices described herein do not necessarily displace, push or reduce the adjacent bone surfaces.

Figure 1B:
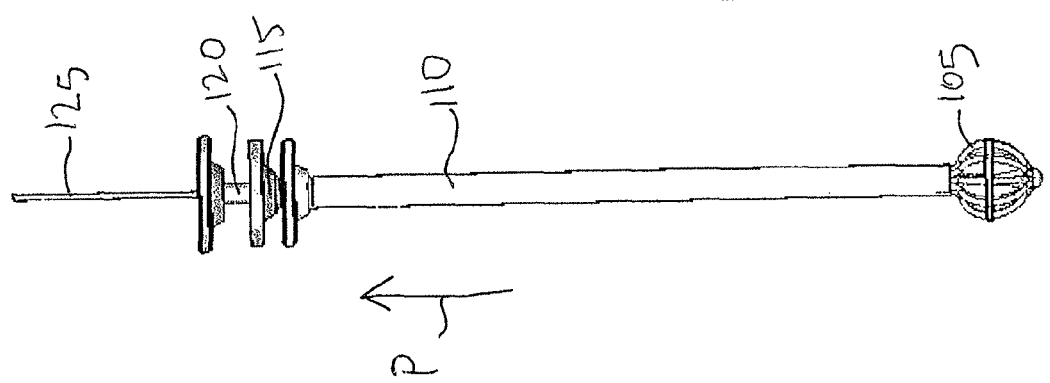
FIGS. 1A-1B show side views of an embodiment of an interbody fusion device and system.
Figure 1A:
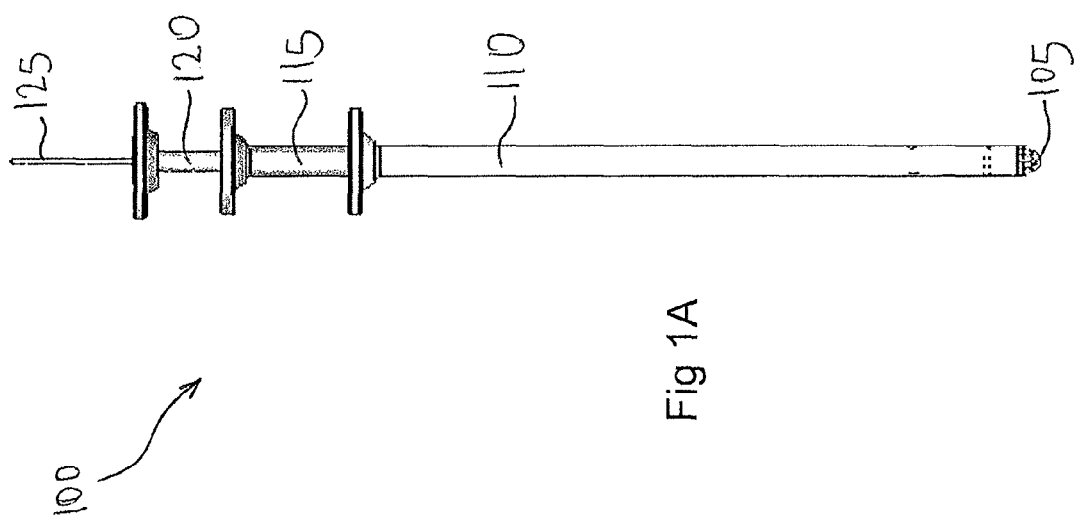

Now with respect to the figures, specific embodiments of an expanding interbody device and fusion system will be described. FIGS. 1A and 1B show side views of an embodiment of an expanding interbody device and fusion system 100. The system 100 can include an interbody device 105 attached to the distal end of a central guidewire or pin 125. The interbody device 105 and pin 125 can extend longitudinally through a containment sleeve 110. The containment sleeve 110 can be a hollow, cylindrical sheath that provides circumferential, inward force on the external surface of the interbody device 105 such that it is retained in a low profile, collapsed state such as, for example, for insertion (see FIG. 1A). Withdrawal of the containment sleeve 110 in the proximal direction (arrow P of FIG. 1B) frees the interbody device 105 to relax into its expanded state as will be discussed in more detail below. The interbody device 105 is generally self-expanding upon removal of the compressive forces of the retaining ring or sheath. It should be appreciated, however, that active expansion techniques or mechanisms can be applied to supplement or replace the self-expanding capabilities of the device 105.

The control sleeve 115 can also insert through the internal lumen of the containment sleeve 110. As best shown in FIGS. 2A-2C, the control sleeve 115 has an engagement region 205 near its distal end. The engagement region 205 of the control sleeve 115 can reversibly couple to a complementary engagement portion 327 positioned near the proximal end of the interbody device 105 (see, for example, FIGS. 6A-6D). Engagement region 205 can be threaded or have another type of coupling mechanism as is known in the art. The control sleeve 115 in combination with the pin 125 can function to hold the interbody device 105 in its narrow insertion configuration. The control sleeve 115 and the pin 125 can also be used in combination to aid in expansion of the interbody device 105 upon proximal withdrawal of the containment sleeve 110. The locking driver 120 can be inserted through the internal lumen of the control sleeve 115. As will be described in more detail below, the locking driver 120 can include a coupling mechanism 210 near its distal end that allows it to reversibly couple to a locking end cap 330 (shown in FIG. 2C).

As best shown in FIGS. 3A-3C and 4A-4C, the interbody device 105 can include a plurality of flexible arms 305 coupled by one or more flexible, circumferential limit bands 310. The flexible arms 305 can be self-expanding such that upon release of a compressive force they each "relax" into a particular shape. For example, the flexible arms 305 can bow radially outward such that the interbody device 105 assumes a volumetrically-enlarged geometry having a generally spheroid shape. The volumetrically-enlarged geometry of the interbody device 105 is generally characterized by axial foreshortening as the outer dimension radially expands. The flexible arms 305 can be disposed asymmetrically or symmetrically around the central axis of the device 105. The device 105 can have one, two, three, four, five or more pairs of flexible arms 305 that can be disposed symmetrically or asymmetrically around the central axis of the device 105. The device 105 can also include three, five, seven, nine or more flexible arms 305 disposed symmetrically or asymmetrically around the central axis of the device 105.

The radially-expanded flexible arms 305 can provide the interbody device 105 with a "defining" perimeter having various shapes. The shape of the expanded device 105 can vary depending on the working space or region in which the device will be expanded and/or released. As mentioned, the flexible arms 305 can bow radially outward from the central axis of the device 105 such that the expanded device 105 takes on a spheroid shape. The flexible arms 305 can also expand outward such that a port of the flexible arms 305 is bent to a certain angle given the device 105 a more angular shape. The expanded flexible arms 305 can provide the device 105 with a fusiform, cylindrical, tubular, oblong, spheroid, umbrella, oval, wedge, cone, triangular, half-moon, or other shape that can be symmetrical or asymmetrical. The embodiment shown in the figures is a generally fusiform-shaped, thin-walled, discontinuous "cage."

Figure 1C:
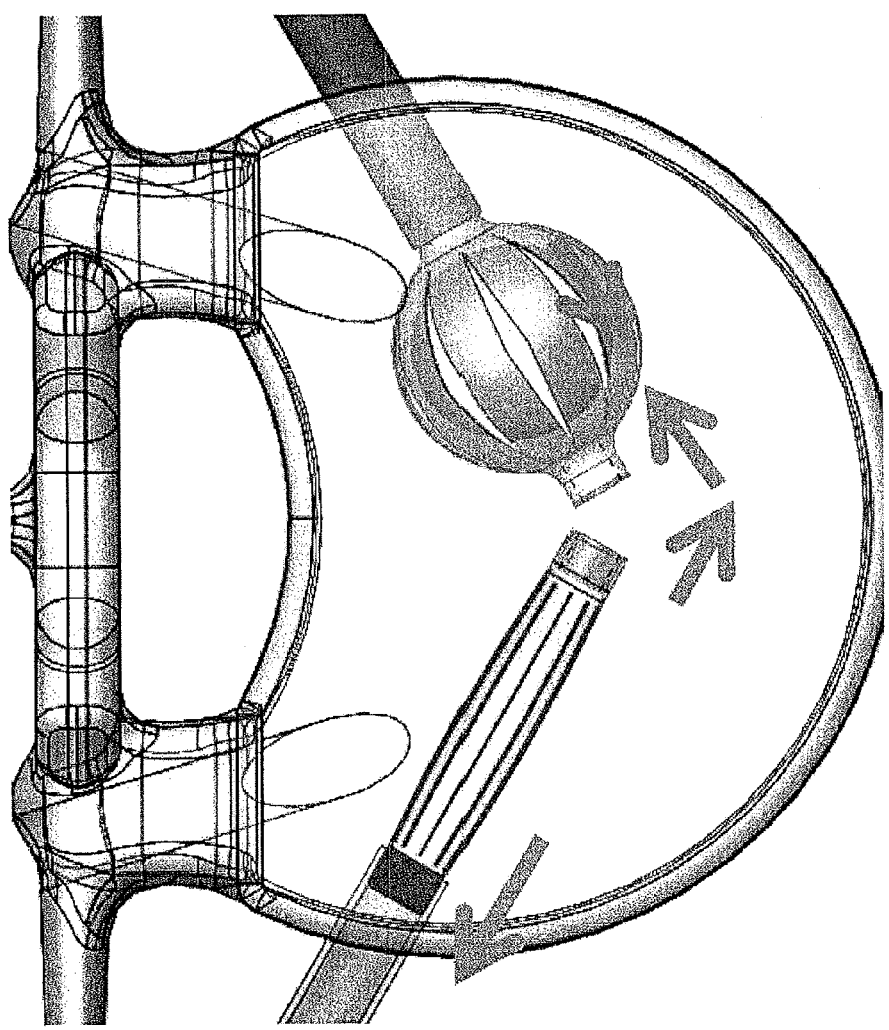
FIG. 1C shows an embodiment of an interbody device transitioning from a radially contracted, axially elongated configuration to a radially expanded, axially shortened configuration.
Figure 4C:
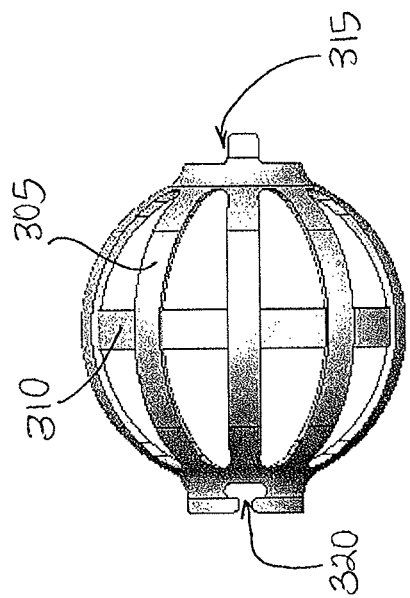
FIGS. 4A-4C show perspective, front and side views of the interbody device of FIGS. 3A-3C in a radially expanded, axially shortened configuration.
Figure 4B:
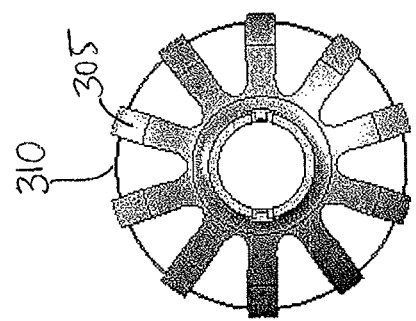
Figure 4A:
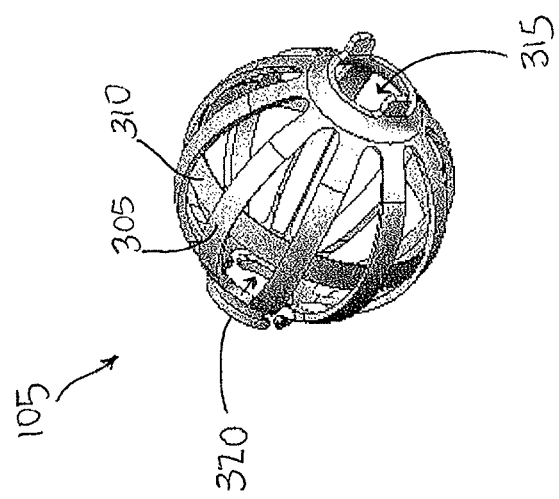

The surface geometry of the interbody device 105 is generally discontinuous. Each of the flexible arms 305 can have a width such that a space is formed between them upon expansion. The width of the flexible arms 305 and the width of the space between the arms 305 can vary. In an embodiment, each of the flexible arms has a width that is between about 0.5 mm and 3 mm. The flexible arms can have a thickness that is between about 0.25 mm and 1.5 mm. In an embodiment, the flexible arms 305 have a width and a portion of each flexible arm overlaps with an adjacent flexible arm 305 such that when in a collapsed state the overall diameter of the device 105 is minimized. The flexible arms 305 can be made thicker or thinner to achieve a particular strength for a particular purpose. Each of the flexible arms 305 can have a wider, more flattened configuration such as shown in the embodiment of FIG. 1C. Each of the flexible arms 305 can also have a more rounded wire-like configuration such as that of FIG. 7. The wall thickness and width of the flexible arms 305 can be uniform or non-uniform. The shape of the flexible arms 305 can provide a specific overall configuration to the interbody device 105. For example, the flexible arms 305 can form a cage, whisk, coil, spring, chain-link, woven basket, or "Chinese finger trap", configuration.

The limit band 310 provide stability to the expanded arms 305 such that the flexible arms 305 are prevented from splaying apart under combined radially- and/or tangentially-directed loads from adjacent vertebrae. The limit band 310 can improve the capacity of the interbody device 105 to resist lateral wall loads. One or more limit bands 310 can be coupled to various circumferential latitudes between the proximal and distal ends of the flexible arms 305. The one or more limit bands 310 can be integral with the flexible arms 305 or can be a separate component affixed to the outer perimeter of the interbody device (see FIGS. 6A-6D). In the latter embodiment, the limit band 310 can have one or more clasps that grip at least a portion of the flexible arms 305 on the inner or outer surface. The one or more limit bands 310 can be coupled to an inner side of the flexible arms 305 such that the bands 310 are positioned within the inner diameter of the device 105. The one or more limit bands 310 can also be coupled between each flexible arm 305. The limit band 310 can also be a plurality of segments that interlink two or more of the flexible arms 305 to prevent splaying between the arms 305. The limit band 310 can have a wider, more flattened configuration such as shown in the embodiment of FIG. 5C. The limit band 310 can also have a more rounded wire-like configuration. The portion of the flexible arms 305 that is in contact or fused to the limit band 310 can have a reduced thickness and/or a specific width such that in the radially contracted position the inward folding of the limit band 310 is accommodated and the external diameter of the device along its axial length is relatively constant.

Both the flexible arms 305 as well as the circumferential limit bands 310 can be self-expanding. The interbody devices described herein can be constructed of biocompatible memory-shaped alloy (e.g. Nitinol, titanium/nickel alloy, nitinol wire mesh) with or without radiolucent material (e.g. PEEK®, Victrex Corp., PolyEtherEtherKetone, or other polymer material). Use of both radiodense and radiolucent elements within the interbody devices provide enhanced mechanical performance while affording improved radiologic monitoring of interosseous bone healing. Also considered is a tubular device having a wall composed of bias ply or meshed material (e.g. polymer strand, or wire strand) with a confining distal wall and an initially open proximal end such that when stretched or in an elongate state its diameter is reduced. In an embodiment, the arms 305 and/or limit bands 310 are manufactured by laser cutting a nitinol tube as is known in the art. The tubular device can also be manufactured of a material including platinum, gold, palladium, rhenium, tantalum, tungsten, molybdenum, rhenium, nickel, cobalt, stainless steel, Nitinol, and alloys thereof.

As the interbody device 105 radially expands upon retraction of the containment sleeve 110 it also axially foreshortens. In the unexpanded configuration the arms 305 are radially collapsed providing the device 105 with a generally cylindrical and axially-elongated shape having a proximal opening 315 and a distal opening 320 (see FIGS. 1A, 3A-3C and 5B). This shape allows the interbody device 105 to fit within the relatively small inner diameter of the containment sleeve 110 for delivery through a working channel into a bone void or evacuated intervertebral disc space. When the device 105 is in the unexpanded configuration, the limit band 310 can buckle or fold inward to form a series of generally undulating links between the arms 305 within the inner diameter of the device 105 (see FIG. 3B). If the limit band 310 is coupled to an outer surface of the flexible arms 305, the limit band 310 can buckle inward through the space between each flexible arm 305 to be positioned within the inner diameter. Upon withdrawal of the containment sleeve 110 or other compressive mechanism, the interbody device 105 can relax into its expanded state (see FIGS. 1B, 4A-4C and 5C). The arms 305 expand radially outward and move further apart such that the serpentine links of the limit band 310 unfold to form a generally circumferential ring connecting the arms 305 along one or more latitudes.

In addition to the limit band 310, the interbody device 105 can have other stabilizing features. In an embodiment, the interbody device 105 can be locked in the radially-expanded configuration. A mechanical coupling can be created to provide a "bowstring" effect that reinforces the expanded interbody device 105 to withstand radially-directed compressive loads. As best shown in FIGS. 5A-5D, the interbody device 105 can include a linkage element 325 and an end cap 330. The linkage element 325 can extend through the interior of the interbody device 105 from the proximal opening 315 to the distal opening 320. The linkage element 325 can be a tension band, screw or other "bowstring" type element. The linkage element 325 can have an engagement portion 335 near its proximal end and a nose piece 340 near its distal end. The distal end of the nose piece 340 can have various shapes, including a pointed or bullet-shaped or other shape. The end cap 330 can be inserted through the containment sleeve 110 into the proximal opening 315 of the interbody device 105. The end cap 330 can have an engagement portion 345 near its distal end that is complementary to the engagement portion 335 of the linkage element such that it mechanically links the proximal and distal ends of the interbody device 105 via the linkage element 325. The nose piece 340 of the linkage element 325 can attach to the interbody device 105 at its distal opening 320. The engagement portion 335 of the linkage element 325 can couple together with the complementary engagement portion 345 of the end cap 330. The mechanical coupling between the linkage element 325 and end cap 330 provides structural enhancement and improves the capacity of the interbody device 105 to resist lateral wall loads or compressive loads directed perpendicular to the long central axis of the interbody device 105 (e.g. radially-directed loads). These loads result in a tensile load on the linkage element 325 fixing the proximal 315 and distal 320 ends of the device 105.

Although the engagement portion 335 of the linkage element 325 and the engagement portion 345 of the end cap 330 are shown as being threaded it should be appreciated that other coupling mechanisms between the linkage element 325 and the end cap 330 are considered. The mechanical coupling between the end cap 330 and the linkage element 325 can also be used to further approximate the proximal to the distal ends of the device 105 providing additional radial expansion and axial foreshortening of the interbody device 105 during locking.

Figure 5B:
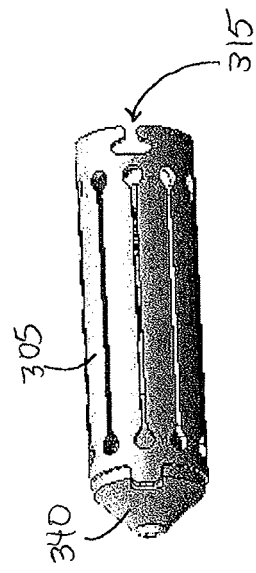
FIG. 5B shows a perspective view of the linkage element and locking end cap positioned within an interbody device.
Figure 5D:
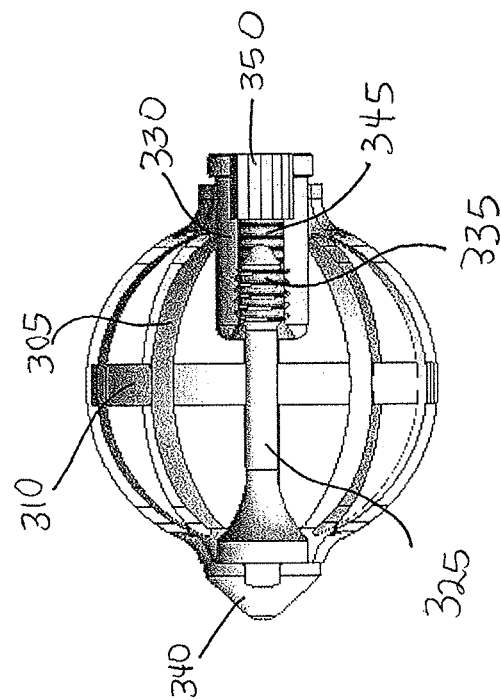
FIG. 5D shows a partial, cross-sectional view of the interbody device of FIG. 5C.
Figure 5A:
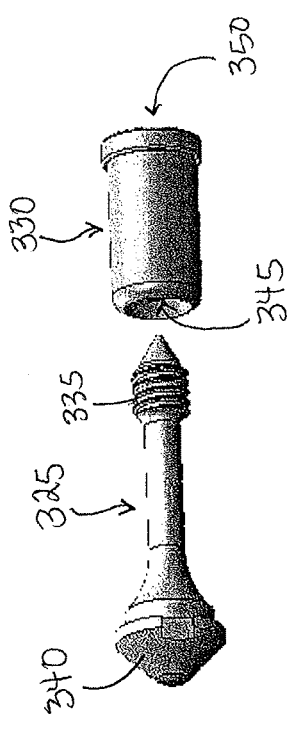
FIG. 5A shows a perspective view of an embodiment of a linkage element and a locking end cap.
Figure 5C:
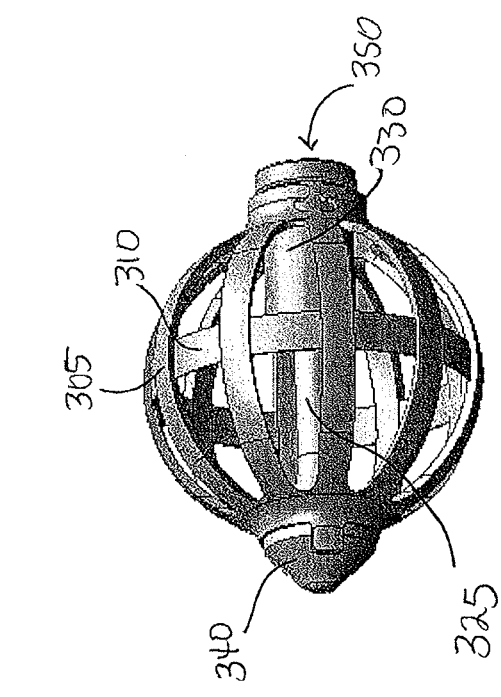
FIG. 5C shows a perspective view of the interbody device of FIG. 5B in a radially expanded and tension locked configuration.
Figure 6B:
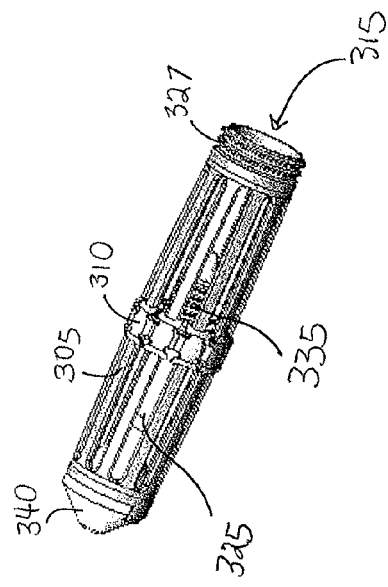
FIG. 6B shows a perspective view of the interbody device of FIG. 6A in a radially contracted configuration.
Figure 6D:
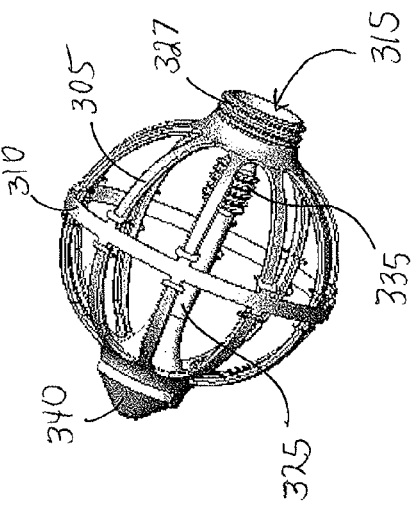
FIG. 6D shows a perspective view of the interbody device of FIG. 6A in a radially expanded configuration.
Figure 6A:
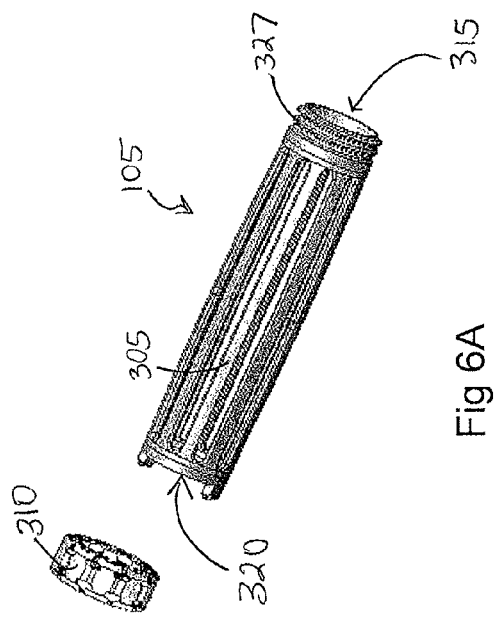
FIG. 6A shows an exploded, perspective view of another embodiment of an interbody device in a radially contracted configuration.
Figure 6C:
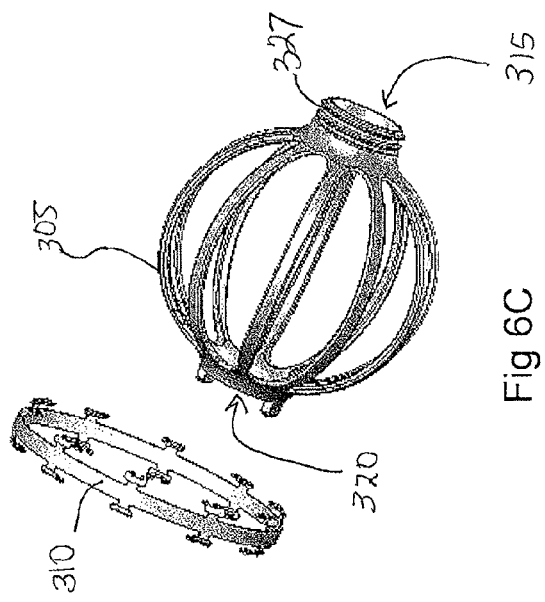
FIG. 6C shows an exploded, perspective view of the interbody device of FIG. 6A in a radially expanded configuration.

As shown best in FIG. 5D, the end cap 330 can include a proximal hex region 350 in addition to the distal engagement portion 345. As mentioned above, the coupling mechanism 210 of the locking driver 120 (e.g. a hex head) can reversibly couple to a complementary proximal region 350 of the end cap 330. The coupling mechanism 210 can engage the complementary hex region 350 of the end cap 330 and screw the end cap 330 into threaded engagement with the engagement portion 335 of the linkage element 325. It should be appreciated that other engagement mechanisms between the locking driver 120 and the end cap 330 are considered.

Figure 7:
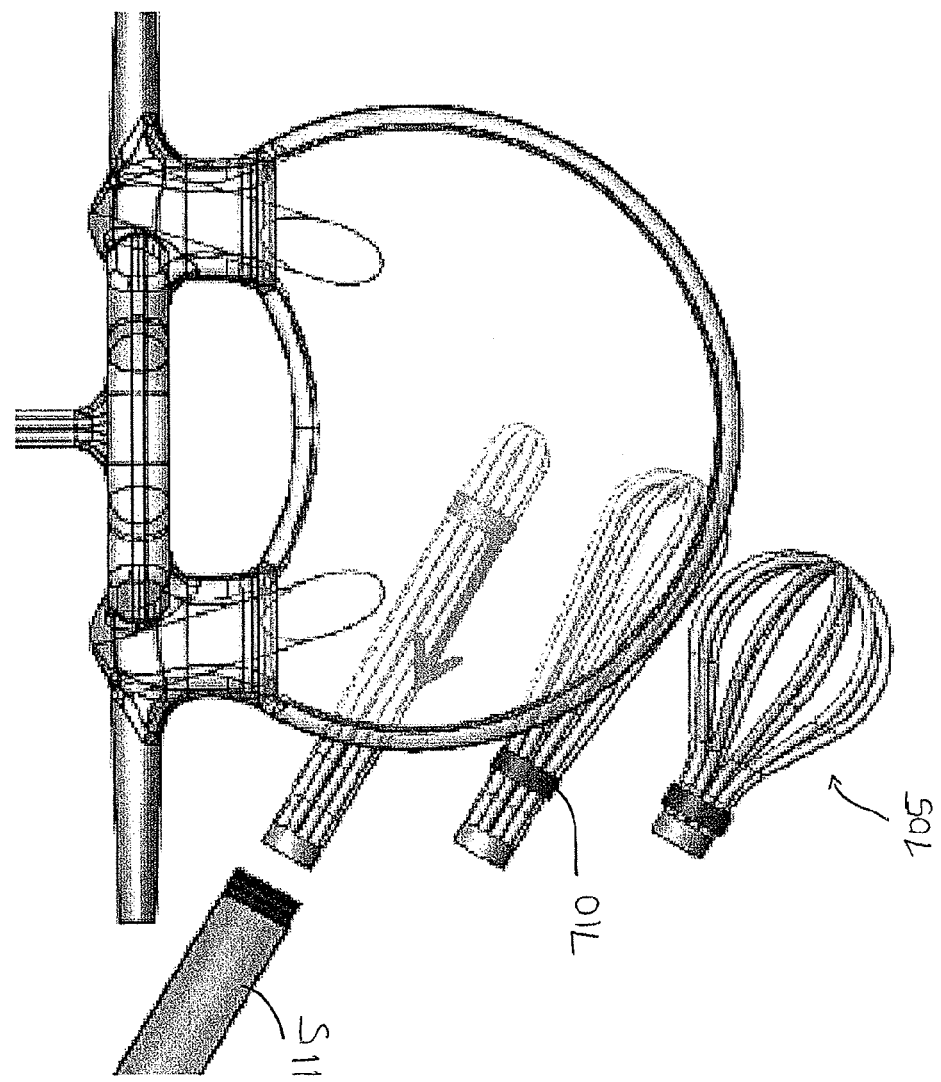
FIG. 7 shows another embodiment of an interbody device transitioning from a radially contracted, axially elongated to a radially expanded, axially shortened configuration.

FIG. 7 shows an embodiment of an expanding interbody device 705 having a whisk-like configuration. In this embodiment, the system uses a slidable retaining ring 710 instead of a containment sleeve 110 to keep the interbody device 705 in the collapsed state for delivery. In the delivery conformation, the retaining ring 710 is near the distal end of the device 705 such that the flexible elements are in close approximation with one another. To expand the device 705, the retaining ring 710 can be moved proximally in the direction of the arrow such that the flexible elements are free to bow radially outward. The mechanism by which the retaining ring 710 is moved can vary as is known in the art.

In the "relaxed" expanded state, portions of the external surface of the interbody devices described herein generally approximate, contact and/or conform to the prepared endplates. Once radially expanded, material can be introduced within and potentially through the voids of the discontinuous walls of the interbody devices described herein to provide for interbody fusion (i.e. stuffed interbody cage technique), in its final form. Exemplary material include bone growth material, bone graft material, bone void filler, cancellous or cortical bone graft, cancellous or cortical bone fragments, osteoconductive, osteoproliferative, and/or osteoinductive material, bone morphogenic cytokines, BMP-2, collagen sponge soaked in bone materials, and BMP-2 soaked collagen sponge.

As shown in FIG. 8, filler material 805 can be delivered through a delivery cannula such as the containment sleeve 110 or control sleeve 115 into the internal volume of the expanded interbody device 105 and, in part, through the voids of the now "relaxed" device 105. The association or coupling of the linkage element 325 with the end cap 330 "seals" the distal and/or proximal end(s) of the interbody device 105 prevents or minimizes the subsequent displacement of inserted materials such as osteoinductive and/or osteoproliferative material from within the general confines of the internal chamber of the interbody fusion device. The filler 805 can be delivered along the axis of introduction from within a delivery cannula into the interior of the expanded interbody device 105. This provides for bone growth from the areas immediately adjacent to the external perimeter of the device 105 into and through the relaxed device 105. Further, a displacing element can be inserted to radially displace the material resulting in distribution of the filler within and through the expanded peripheral elements of the interbody device. It should be appreciated that the filler 805 is not generally used to deform or radially expand the interbody device 105 nor does it necessarily provide supplemental structural support.

Once the interbody device 105 is expanded, optionally filled with a desired compound or material, and locked, it can be releasably deployed. The locking driver 120 can be withdrawn proximally. The engagement region 205 near the distal end of the control sleeve 115 can be unscrewed, rotated and/or pulled or otherwise disengaged from the proximal, complementary engagement portion 327 of the interbody device 105. The coupling region can be a simple thread form, a bayonet style locking mechanism, pull lock or other interference fit or friction lock. The adjacent endplates can engage and hold the device 105 in position such that the device 105 can be uncoupled from components of the delivery system. The pin 125 can also function to hold the interbody device 105 during the release and deployment of the components of the delivery system or counter a simple pull lock that relied upon an interference fit or friction lock. Once uncoupled from the proximal end of the device 105, the containment sleeve 110, control sleeve 115 and pin 125 can be withdrawn proximally leaving the interbody device 105 deployed within the intervertebral disc space.

Optionally, the interbody device 105 can be reduced to its pre-expanded configuration and removed. The end cap 330 can be removed from mechanical linkage with the linkage element 325. The pin 125 or other axially-deployed element can then be advanced to displace the linkage element 325 in a distal direction while the proximal end of the device 105 is restrained, such as with the control sleeve 115. The interbody device 105 is in turn elongated axially and radially contracted such that it can be withdrawn proximally back into a containment sleeve 110.

Methods of Use

As mentioned above, the interbody devices and fusion systems described herein are designed for minimally-invasive interbody fusion procedures and can be deployed through a variety of minimally-invasive access channels (TLIF, ITLIF™, ITSLIF, EXLIF™, DLIF™, ALIF, PLIF, etc.).

The interbody devices described herein can be used for a variety of surgical applications in which an interosseous space exists in an initially collapsed or approximated condition and therapeutic intervention includes distracting the interosseous space with subsequent stabilization (e.g. a degenerative intervertebral disc space). The interbody devices can be deployed into evacuated intervertebral disc spaces, for example, following removal of disc material and excoriation of the endplates. Another potential application for the interbody devices and fusion systems described herein is for the treatment of an existing or created bone defect, such as might occur in a bone cyst or reduced fracture. This application as well as others could be deployed via percutaneous methods via a delivery cannula(s).

An exemplary method of using the system is now described. At least one pathway can be formed in the patient to provide access to the disc space to be treated. Various methods and devices can be used to form the at least one pathway. The disc space can be a prepared disc space such as a partially-vacated disc space. In an embodiment, a pair of intraosseous transpedicular pathways can be formed wherein each pathway provides a portal into the disc space. In an embodiment, access pathways are formed on either side of the disc's mid-sagittal plane. The pathways can be formed pursuant to the methods and devices described in for example as described in U.S. Patent Application Publication Nos. 2007-0162044, 2009-0312764, and U.S. patent application Ser. No. 12/778,057, filed May 11, 2010, which are each incorporated by reference herein in their entirety by reference thereto. The figures illustrate the anatomic landmarks in the spine and access through the vertebrae to the intervertebral disc space in schematic. Those skilled in the art will appreciate that actual anatomy include anatomical details not shown in the figures.

Figure 9A:
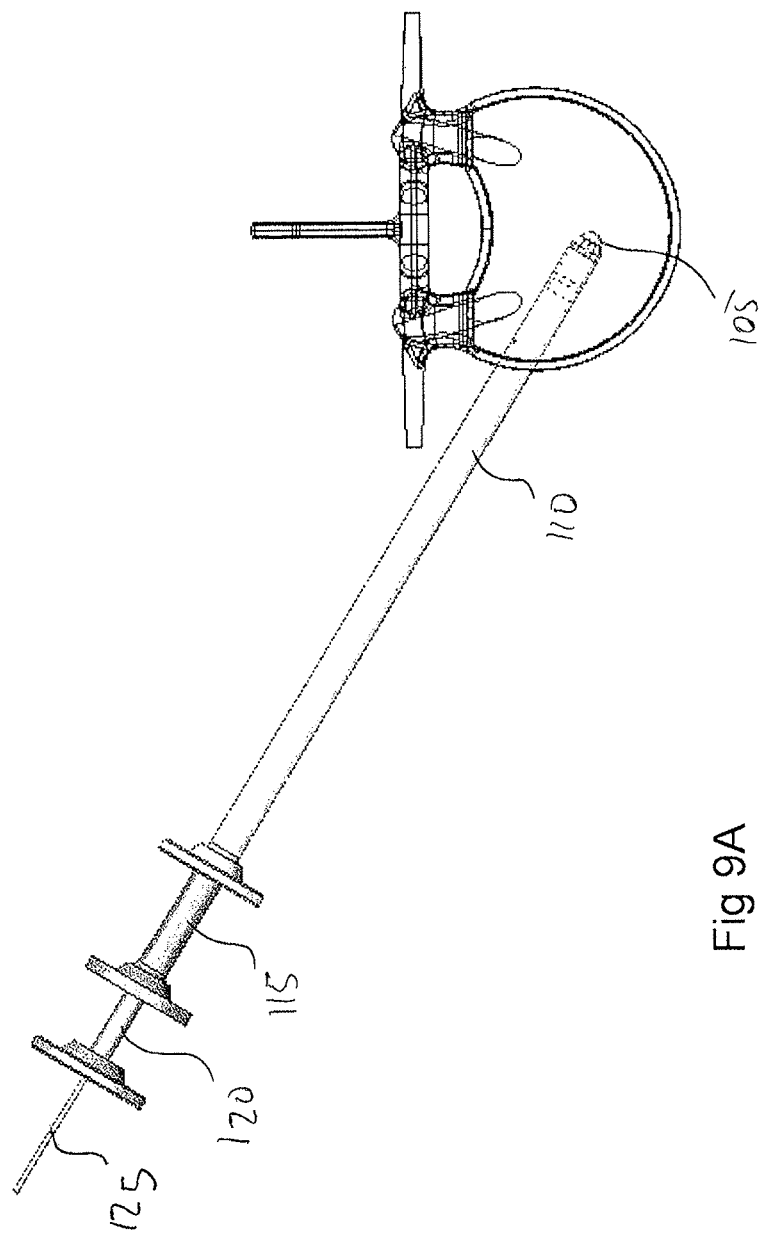
FIGS. 9A-9C illustrates an exemplary method of use of an embodiment of an interbody fusion device and system.
Figure 9B:
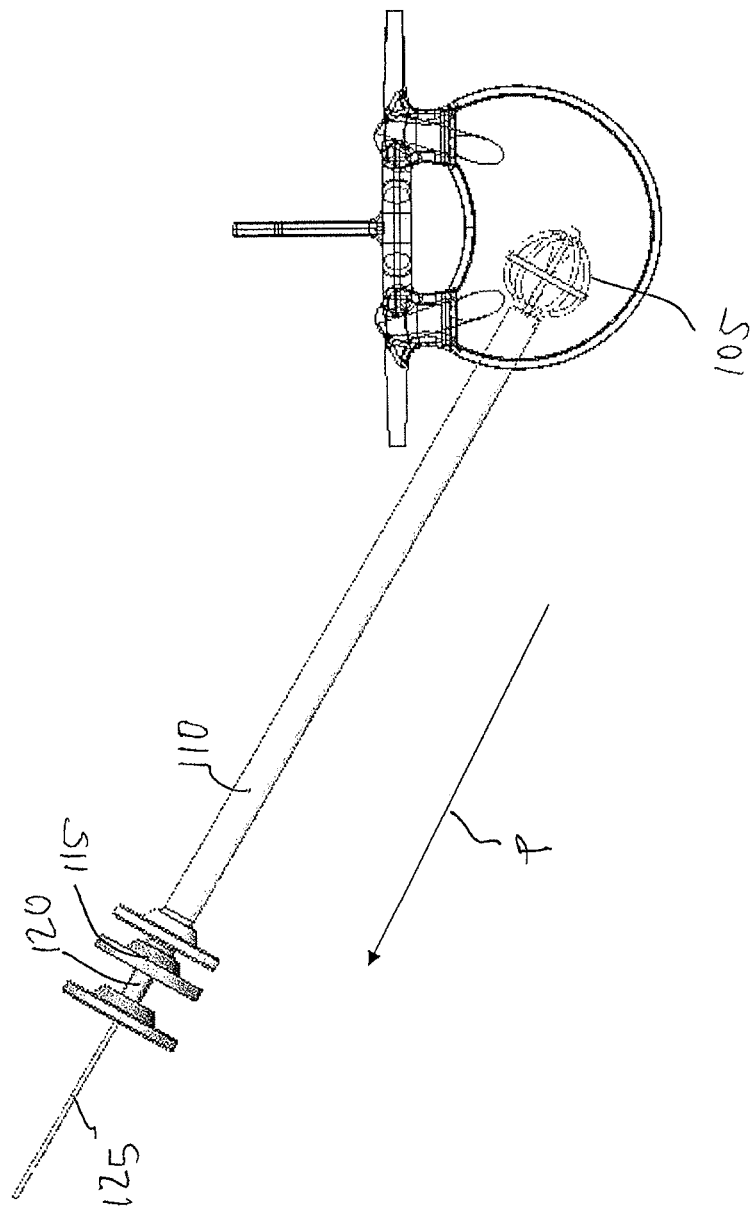

Once the pathways are formed, the interbody device 105 can be actively compressed within the containment sleeve 110 of the system 100 to achieve a radially contracted, axially elongated configuration suitable for insertion into a bone void. FIG. 9A shows an embodiment of the interbody device 105 positioned in the intraosseous transpedicular pathway to the disc space. Once in proper position, the pin 125 and control sleeve 115 can be urged in a slightly distal direction to stabilize the position of the interbody device 105 as the containment sleeve 110 is retracted in the proximal direction (arrow P in FIG. 9B). The interbody device 105 is exposed through the distal end of the containment sleeve 110 and allowed to relax into a radially expanded, axially foreshortened configuration. The flexible arms 305 can relax outward and the undulated limit band 310 can unfold into a generally circumferential ring providing stability against splay of the arms 305.

Figure 9C:
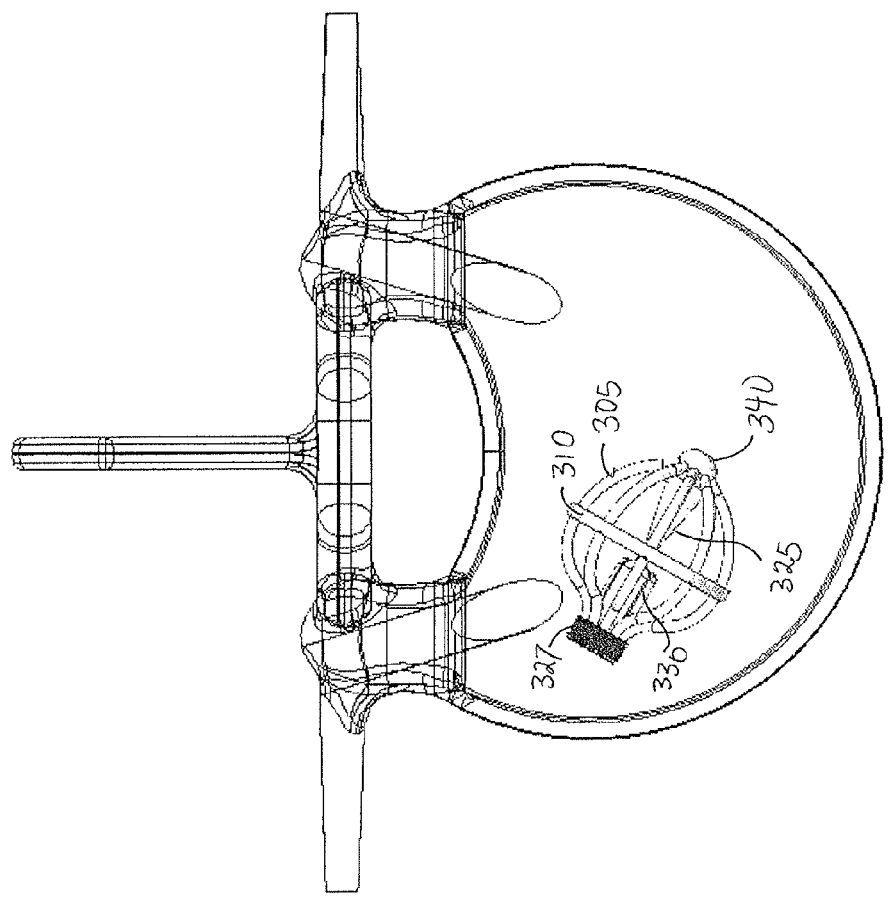

The nose bullet 340 (see FIG. 9C) of the linkage element 325 extending through the interior of the interbody device 105 can be coupled to the distal opening 320 of the interbody device 105. The locking end cap 330 can be inserted through the control sleeve 115 using the locking driver 120. The locking driver 120 can be rotated such that the hex head of the locking driver 120 engages the hex region at the proximal region of the end cap 330. As the end cap 330 is rotated by the locking driver 120, the engagement portion 345 of the end cap 330 couples to the complementary engagement portion 335 of the linkage element 325. The mechanical coupling between the linkage element 325 and the end cap 330 provides structural enhancement and improves the capacity of the interbody device 105 to resist lateral wall loads or compressive loads directed perpendicular to the long central axis of the interbody device 105. The loads result in a tensile load on the linkage element 325 and the end cap 330 therein locking the distal and proximal ends of the interbody device 105 in the axially foreshortened configuration.

The coupling of the linkage element 325 and end cap 330 to the interbody element 105 also seals the proximal and distal openings 315, 320 such that bone growth material or another type of therapeutic filler material can be infused into the void or interior of the interbody device 105. Once the interbody device 105 is tensioned, locked and optionally filled with a desired compound or material it can be released such as by unscrewing the distal end of the control sleeve 115 from the proximal end of the interbody device 105 and deployed within the target treatment location, such as a bone void or evacuated intervertebral disc space (see FIG. 9C).

Methods of Manufacture

Spinal stabilization devices described herein can be manufactured according to methods known in the art. In an embodiment, the manufacture of the device includes providing a tubular element having an inner passageway and an axial length. The tubular element can be a single, monolith of tubular material or a sheet of material in which the ends are coupled together to form a tube. The tubular element can be made of a shape memory material or other material as is known in the art. A laser system can be used to remove portions of the tubular element using cut lines parallel to the longitudinal axis or axial length of the tubular element. For example, laser vaporization or machining techniques can be used as is known in the art. The cut lines can extend through the total thickness of the tubular element such that portions are removed and openings through the tubular element defined. This creates a plurality of elongate, axially-aligned flexible arms surrounding the inner passageway having a first thickness and a plurality of spaces between the arms. The pattern of arms created can vary as described above.

The laser system can also be used to remove a layer or layers of material from the arms using cut lines that are transverse to the elongate axis or axial length of the tubular element. In this embodiment, the cut or score lines extend through less than the total radial thickness of the wall of the tubular element. This removes the layer or layers of material and creates regions of the arms having a second thickness that is thinner than the first thickness.

The tubular element can be manufactured of a shape memory material such as nitinol, titanium/nickel alloy or a polymeric material, as described above. The shape memory of the tubular element can be shaped and heat-set when in the radially expanded, axially foreshortened configuration. In an embodiment, the device is nitinol material and possesses super-elastic properties generally at body temperature. The tubular element can then be compressed and cooled into a radially contracted, axially elongated configuration. As such, the arms of the tubular element can self-expand upon release of a constraining force into the radially expanded, axially foreshortened stabilization configuration.

A flexible, limit band for the prevention of arm splaying can be coupled circumferentially to the regions of the arms having the second thickness. The band can be welded to the arms once in the expanded configuration. Alternatively, the limit band can be created as the flexible arms are created by making cut lines with the laser system such that cuts are made that go through the full thickness of the tubular element forming the pattern of elongate arms that are aligned with the longitudinal axis of the tubular member and bridging elements that are transverse to the longitudinal axis of the tubular member that extend between the elongate arms. This non-uniform wall thickness of the flexible arms allows the areas in contact with or fused to the limit band to have a relatively constant external diameter when in the radially contracted configuration and accommodate the inward folding of the peripheral limit band.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A spinal stabilization device, the device comprising:
a plurality of elongate arms having a distal end portion and a proximal end portion, wherein the elongate arms define an interior volume between the distal end portion and the proximal end portion;
a limit band coupled circumferentially to the plurality of elongate arms; and
a tensioning element positioned within the interior volume, wherein the interior volume is filled with one or more therapeutic materials;
wherein the plurality of elongate arms passively transition from a constrained, delivery configuration that is radially contracted and axially elongated to a relaxed, deployment configuration that is radially expanded and axially shortened and configured to be released within an intervertebral disc space.

2. The device of claim 1, wherein the limit band is integral with one or more of the plurality of elongate arms.

3. The device of claim 1, wherein the limit band is a separate unitary element coupled to an outer circumference of the device.

4. The device of claim 1, wherein the limit band is radially contracted when the plurality of elongate arms are in the delivery configuration and the limit band is radially expanded when the plurality of elongate arms are in the deployment configuration.

5. The device of claim 1, wherein the limit band resists splaying of the plurality of arms when in the deployment configuration and the device is under a lateral wall load.

6. The device of claim 1, the tensioning element comprises a linkage rod and a locking end cap.

7. The device of claim 6, wherein the linkage rod comprises a distal end and a proximal end, wherein the distal end of the linkage rod couples to the distal end portion of the elongate arms and the proximal end of the linkage rod couples to the locking end cap.

8. The device of claim 7, wherein the locking end cap is coupled to the proximal end portion of the elongate arms.

9. The device of claim 8, wherein the tensioning element locks the distal end portion of the arms and the proximal end portions of the arms when the arms are in the deployment configuration.

10. The device of claim 8, wherein compressive loads directed perpendicular to the elongate arms result in a tensile load on the tensioning element.

11. The device of claim 7, wherein the proximal end of the linkage rod is threaded and couples to complementary threads of the locking end cap.

12. The device of claim 1, wherein an applied circumferential, inward force urges the plurality of arms into the delivery configuration.

13. The device of claim 1, wherein the interior volume in the deployment configuration comprises a fusiform, tubular, oblong, or spheroid shape.

14. The device of claim 1, wherein the deployment configuration of the plurality of elongate arms comprises a whisk, coil, spring, chain-link, or woven basket shape.

15. The device of claim 1, wherein the therapeutic materials are selected from the group consisting of bone growth material, bone graft material, bone void filler, cancellous bone graft, cortical bone graft, cancellous bone fragment, cortical bone fragment, osteoconductive material, osteoproliferative material, osteoinductive material, a bone morphogenic cytokine, BMP-2, collagen sponge soaked in bone material, or BMP-2 soaked collagen sponge.

16. The device of claim 1, wherein the tensioning element seals the interior volume at the distal end portion and the proximal end portion.

17. The device of claim 1, wherein the tensioning element radially displaces and distributes the therapeutic material within the interior volume.

18. The device of claim 1, wherein the plurality of elongate arms is comprised of a material selected from the group consisting of nitinol, titanium/nickel alloy, and a polymeric material.

19. The device of claim 1, wherein the plurality of elongate arms have a wall thickness that is non-uniform.

20. The device of claim 1, wherein the plurality of elongate arms have a width that is non-uniform.

21. The device of claim 1, wherein the plurality of elongate arms have a reduced wall thickness where the arms couple to the limit band.

22. The device of claim 1, wherein the plurality of elongate arms have a reduced width where the arms couple to the limit band.

23. The device of claim 1, wherein an external diameter of the device in the constrained, delivery configuration is generally constant.

24. A vertebral interbody fusion system comprising:
an interbody device comprising a plurality of elongate arms having a distal end portion and a proximal end portion, wherein the elongate arms define an interior volume between the distal end portion and the proximal end portion of the interbody device, and at least one limit band coupled circumferentially to one or more of the plurality of elongate arms, the interbody device capable of transitioning from a constrained, delivery configuration that is radially contracted and axially elongated to a relaxed, deployed configuration that is radially expanded and axially shortened;
a tensioning element positioned within the interior volume, the tensioning element comprising a linkage rod and a locking end cap; and
a cannula assembly configured to couple to the interbody device, the cannula assembly comprising a slidable containment sleeve having a lumen sized to contain the interbody device in the delivery configuration, a control sleeve having a distal coupling element that couples to the proximal end portion of the interbody device, and a locking driver element;
wherein the interbody device transitions from the delivery configuration to the deployed configuration upon proximal withdrawal of the containment sleeve.

25. The system of claim 24, wherein the limit band is integral with one or more of the plurality of elongate arms.

26. The system of claim 24, wherein the limit band is a separate unitary element coupled to an outer circumference of the device.

27. The system of claim 24, wherein the limit band is radially contracted when the plurality of elongate arms are in the delivery configuration and the limit band is radially expanded when the plurality of elongate arms are in the deployed configuration.

28. The system of claim 24, wherein the limit band resists splaying of the plurality of arms when in the deployed configuration and the device is under a lateral wall load.

29. The system of claim 28, wherein the linkage rod comprises a distal end and a proximal end, wherein the distal end of the linkage rod couples to the distal end portion of the elongate arms and the proximal end of the linkage rod couples to the locking end cap.

30. The system of claim 29, wherein the locking end cap is coupled to the proximal end portion of the elongate arms.

31. The system of claim 30, wherein the tensioning element locks the distal end portion of the arms and the proximal end portions of the arms when the arms are in the deployed configuration.

32. The system of claim 30, wherein compressive loads directed perpendicular to the elongate arms result in a tensile load on the tensioning element.

33. The system of claim 29, wherein the proximal end of the linkage rod is threaded and couples to complementary threads of the locking end cap.

34. The system of claim 24, wherein the slidable containment sleeve applies a circumferential, inward force upon the plurality of arms when in the delivery configuration.

35. The system of claim 24, wherein proximal withdrawal of the slideable containment sleeve removes the circumferential, inward force on the plurality of arms.

36. The system of claim 24, wherein the interior volume in the deployed configuration comprises a fusiform, tubular, oblong, or spheroid shape.

37. The system of claim 24, wherein the deployed configuration of the plurality of elongate arms comprises a whisk, coil, spring, chain-link, or woven basket shape.

38. The system of claim 24, wherein the interior volume is filled with one or more therapeutic materials.

39. The system of claim 38, wherein the therapeutic materials are selected from the group consisting of bone growth material, bone graft material, bone void filler, cancellous bone graft, cortical bone graft, cancellous bone fragment, cortical bone fragment, osteoconductive material, osteoproliferative material, osteoinductive material, a bone morphogenic cytokine, BMP-2, collagen sponge soaked in bone material, or BMP-2 soaked collagen sponge.

40. The system of claim 38, wherein the tensioning element seals the interior volume at the distal end portion and the proximal end portion.

41. The system of claim 38, wherein the tensioning element radially displaces and distributes the therapeutic material within the interior volume.

42. The system of claim 24, wherein the plurality of elongate arms is comprised of a material selected from the group consisting of nitinol, titanium/nickel alloy, and a polymeric material.

43. The system of claim 24, wherein the cannula assembly is configured to reversibly couple to the interbody device.

44. The system of claim 24, wherein the distal coupling element of the control sleeve reversibly couples to the proximal end portion of the interbody device.

45. A spinal stabilization device, the device comprising:
a plurality of elongate arms having a distal end portion and a proximal end portion, wherein the elongate arms define an interior volume between the distal end portion and the proximal end portion;
a limit band coupled circumferentially to the plurality of elongate arms; and
a tensioning element positioned within the interior volume;
wherein the plurality of elongate arms passively transition from a constrained, delivery configuration that is radially contracted and axially elongated to a relaxed, deployment configuration that is radially expanded and axially shortened and configured to be released within an intervertebral disc space, and wherein the plurality of elongate arms have a reduced wall thickness where the arms couple to the limit band.

46. A spinal stabilization device, the device comprising:

a plurality of elongate arms having a distal end portion and a proximal end portion, wherein the elongate arms define an interior volume between the distal end portion and the proximal end portion;

a limit band coupled circumferentially to the plurality of elongate arms; and a tensioning element positioned within the interior volume;

wherein the plurality of elongate arms passively transition from a constrained, delivery configuration that is radially contracted and axially elongated to a relaxed, deployment configuration that is radially expanded and axially shortened and configured to be released within an intervertebral disc space, and wherein the plurality of elongate arms have a reduced width where the arms couple to the limit band.

* * * * *